(12) United States Patent
Rehm et al.

(10) Patent No.: US 12,246,146 B2
(45) Date of Patent: Mar. 11, 2025

(54) AUTOMATED WEIGHT BASED FLUID OUTPUT MONITORING SYSTEM

(71) Applicant: C. R. Bard, Inc., Franklin Lakes, NJ (US)

(72) Inventors: Eric A. Rehm, Lawrenceville, GA (US); Anthony S. Esposito, Oxford, GA (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 622 days.

(21) Appl. No.: 17/560,079

(22) Filed: Dec. 22, 2021

(65) Prior Publication Data

US 2022/0193375 A1 Jun. 23, 2022

Related U.S. Application Data

(60) Provisional application No. 63/130,301, filed on Dec. 23, 2020.

(51) Int. Cl.
*A61M 25/02* (2006.01)
*A61M 25/00* (2006.01)

(52) U.S. Cl.
CPC ........ *A61M 25/02* (2013.01); *A61M 25/0017* (2013.01); *A61M 2205/3327* (2013.01);
(Continued)

(58) Field of Classification Search
CPC ....... A61B 5/207; A61B 5/208; A61B 10/007; A61B 2560/0223; A61M 25/0017;
(Continued)

(56) References Cited

U.S. PATENT DOCUMENTS 3,661,143 A 5/1972 Henkin
3,781,920 A 1/1974 Browne et al.
(Continued)

FOREIGN PATENT DOCUMENTS

CA 2882654 A1 10/2007
CN 2445749 Y 9/2001
(Continued)

OTHER PUBLICATIONS

EP 20962628.2 filed May 31, 2023 Extended European Search Report dated Apr. 20, 2024.
(Continued)

*Primary Examiner* — Daniel L Cerioni
*Assistant Examiner* — Abel Seifu Abegaz
(74) *Attorney, Agent, or Firm* — Rutan & Tucker LLP

(57) ABSTRACT

Disclosed is an automated weight based fluid output monitoring system that can include a hanger having a securement ball defining a spherical surface and configured to engage a socket. The securement ball can include a sensor array configured to detect a change in pressure between the securement ball and the socket as well as a direction of force relative to a transverse axis of the socket. The hanger can further include a hook configured to be coupled to a fluid collection bag of a fluid drainage system. The hanger can further include a console having one or more processors, non-transitory storage medium, an energy source and a one or more logic modules configured to determine a change in fluid volume of the collection bag over time and an off-axis loading of the fluid collecting bag relative to the transverse axis.

21 Claims, 9 Drawing Sheets

(52) U.S. Cl.
CPC ............... *A61M 2205/3331* (2013.01); *A61M 2205/3379* (2013.01); *A61M 2205/3553* (2013.01); *A61M 2209/084* (2013.01)

(58) Field of Classification Search
CPC .. A61M 2205/3327; A61M 2205/3331; A61M 2205/3334; A61M 2205/3379; A61M 2205/3553; A61M 2205/3561; A61M 2205/3569; A61M 2209/084; A61M 2210/1085
See application file for complete search history.

(56) References Cited

U.S. PATENT DOCUMENTS

| | | |
|---|---|---|
| 3,851,650 A | 12/1974 | Darling |
| 3,919,455 A | 11/1975 | Sigdell et al. |
| 4,276,889 A | 7/1981 | Kuntz et al. |
| 4,286,590 A | 9/1981 | Murase |
| 4,291,692 A | 9/1981 | Bowman et al. |
| 4,296,749 A | 10/1981 | Pontifex |
| 4,305,405 A | 12/1981 | Meisch |
| 4,312,352 A | 1/1982 | Meisch et al. |
| 4,343,316 A | 8/1982 | Jespersen |
| 4,443,219 A | 4/1984 | Meisch et al. |
| 4,448,207 A | 5/1984 | Parrish |
| 4,509,366 A | 4/1985 | Matsushita et al. |
| 4,532,936 A | 8/1985 | LeVeen et al. |
| 4,658,834 A | 4/1987 | Blankenship et al. |
| 4,712,567 A | 12/1987 | Gille et al. |
| 4,723,950 A | 2/1988 | Lee |
| 4,834,706 A | 5/1989 | Beck et al. |
| 4,850,375 A | 7/1989 | Rosenberg |
| 4,889,532 A | 12/1989 | Metz et al. |
| 5,002,541 A | 3/1991 | Conkling et al. |
| 5,409,014 A | 4/1995 | Napoli et al. |
| 5,586,085 A | 12/1996 | Lichte |
| 5,725,515 A | 3/1998 | Propp |
| 5,733,319 A | 3/1998 | Neilson et al. |
| 5,738,656 A | 4/1998 | Wagner |
| 5,747,824 A | 5/1998 | Jung et al. |
| 5,769,087 A | 6/1998 | Westphal et al. |
| 5,807,278 A | 9/1998 | McRae |
| 5,823,972 A | 10/1998 | McRae |
| 5,891,051 A | 4/1999 | Han et al. |
| 5,911,786 A | 6/1999 | Nielsen et al. |
| 6,129,684 A | 10/2000 | Sippel et al. |
| 6,132,407 A | 10/2000 | Genese et al. |
| 6,250,152 B1 | 6/2001 | Klein et al. |
| 6,256,532 B1 | 7/2001 | Cha |
| 6,261,254 B1 | 7/2001 | Baron et al. |
| 6,434,418 B1 | 8/2002 | Neal et al. |
| 6,579,247 B1 | 6/2003 | Abramovitch et al. |
| 6,592,612 B1 | 7/2003 | Samson et al. |
| 6,709,420 B1 | 3/2004 | Lincoln et al. |
| 6,716,200 B2 | 4/2004 | Bracken et al. |
| 7,011,634 B2 | 3/2006 | Paasch et al. |
| 7,161,484 B2 | 1/2007 | Tsoukalis |
| 7,211,037 B2 | 5/2007 | Briggs et al. |
| 7,437,945 B1 | 10/2008 | Feller |
| 7,442,754 B2 | 10/2008 | Tepper et al. |
| 7,739,907 B2 | 6/2010 | Boiarski |
| 7,871,385 B2 | 1/2011 | Levinson |
| 7,931,630 B2 | 4/2011 | Nishtala et al. |
| 7,976,533 B2 | 7/2011 | Larsson |
| 7,998,126 B1 | 8/2011 | Fernandez |
| 8,295,933 B2 | 10/2012 | Gerber et al. |
| 8,328,733 B2 | 12/2012 | Forte et al. |
| 8,328,734 B2 | 12/2012 | Salvadori et al. |
| 8,337,476 B2 | 12/2012 | Greenwald et al. |
| 8,374,688 B2 | 2/2013 | Libbus et al. |
| 8,403,884 B2 | 3/2013 | Nishtala |
| 8,471,231 B2 | 6/2013 | Paz |
| 8,663,128 B2 | 3/2014 | Paz et al. |
| 8,773,259 B2 | 7/2014 | Judy et al. |
| 8,790,277 B2 | 7/2014 | Elliott et al. |
| 8,790,320 B2 | 7/2014 | Christensen |
| 8,790,577 B2 | 7/2014 | Mizumoto et al. |
| 8,813,551 B2 | 8/2014 | Boiarski |
| 8,827,924 B2 | 9/2014 | Paz et al. |
| 8,832,558 B2 | 9/2014 | Cardarelli et al. |
| 8,900,196 B2 | 12/2014 | Andino |
| 9,045,887 B2 | 6/2015 | O'Malley |
| 9,050,046 B2 | 6/2015 | Elliott et al. |
| 9,074,920 B2 | 7/2015 | Mendels et al. |
| 9,216,242 B2 | 12/2015 | Nishtala et al. |
| 9,480,821 B2 | 11/2016 | Ciccone et al. |
| 9,592,034 B2 | 3/2017 | Hall et al. |
| 9,642,987 B2 | 5/2017 | Bierman et al. |
| 9,731,097 B2 | 8/2017 | Andino et al. |
| 9,895,095 B2 | 2/2018 | Chen |
| 9,962,516 B2 | 5/2018 | Lampotang et al. |
| 10,182,747 B2 | 1/2019 | Charlez et al. |
| 10,245,008 B2 | 4/2019 | Paige |
| 10,362,981 B2 | 7/2019 | Paz et al. |
| 10,383,606 B1 | 8/2019 | McCord et al. |
| 10,448,875 B2 | 10/2019 | Holt et al. |
| 10,799,386 B1 | 10/2020 | Harrison, Sr. |
| 10,881,778 B2 | 1/2021 | Scarpaci et al. |
| 11,703,365 B2 | 7/2023 | Tourchak et al. |
| 2001/0056226 A1 | 12/2001 | Zodnik et al. |
| 2002/0016719 A1 | 2/2002 | Nemeth et al. |
| 2002/0161314 A1 | 10/2002 | Sarajarvi |
| 2002/0193760 A1 | 12/2002 | Thompson |
| 2003/0000303 A1 | 1/2003 | Livingston et al. |
| 2003/0163183 A1 | 8/2003 | Carson |
| 2003/0163287 A1 | 8/2003 | Vock et al. |
| 2004/0267086 A1 | 12/2004 | Anstadt et al. |
| 2005/0020958 A1 | 1/2005 | Paolini et al. |
| 2005/0065583 A1 | 3/2005 | Voorhees et al. |
| 2005/0172712 A1 | 8/2005 | Nyce |
| 2005/0247121 A1 | 11/2005 | Pelster |
| 2006/0100743 A1 | 5/2006 | Townsend et al. |
| 2006/0253091 A1 | 11/2006 | Vernon |
| 2007/0010797 A1 | 1/2007 | Nishtala et al. |
| 2007/0106177 A1 | 5/2007 | Hama |
| 2007/0145137 A1 | 6/2007 | Mrowiec |
| 2007/0252714 A1 | 11/2007 | Rondoni et al. |
| 2008/0312556 A1 | 12/2008 | Dijkman |
| 2009/0056020 A1 | 3/2009 | Caminade et al. |
| 2009/0099629 A1 | 4/2009 | Carson et al. |
| 2009/0157430 A1 | 6/2009 | Rule et al. |
| 2009/0287170 A1 | 11/2009 | Otto |
| 2009/0315684 A1 | 12/2009 | Sacco et al. |
| 2010/0094204 A1 | 4/2010 | Nishtala |
| 2010/0130949 A1 | 5/2010 | Garcia |
| 2010/0137743 A1 | 6/2010 | Nishtala et al. |
| 2011/0113540 A1 | 5/2011 | Plate et al. |
| 2011/0120219 A1 | 5/2011 | Barlesi et al. |
| 2011/0178425 A1 | 7/2011 | Nishtala et al. |
| 2011/0224636 A1 | 9/2011 | Keisic |
| 2011/0230824 A1 | 9/2011 | Salinas et al. |
| 2011/0238042 A1 | 9/2011 | Davis et al. |
| 2011/0251572 A1 | 10/2011 | Nishtala et al. |
| 2011/0263952 A1 | 10/2011 | Bergman et al. |
| 2012/0029408 A1 | 2/2012 | Beaudin |
| 2012/0059286 A1 | 3/2012 | Hastings et al. |
| 2012/0078137 A1 | 3/2012 | Mendels et al. |
| 2012/0078235 A1 | 3/2012 | Martin et al. |
| 2012/0095304 A1 | 4/2012 | Biondi |
| 2012/0109008 A1 | 5/2012 | Charlez et al. |
| 2012/0123233 A1 | 5/2012 | Cohen |
| 2012/0127103 A1 | 5/2012 | Qualey et al. |
| 2012/0226196 A1 | 9/2012 | DiMino et al. |
| 2012/0234434 A1 | 9/2012 | Woodruff et al. |
| 2012/0302917 A1 | 11/2012 | Fitzgerald et al. |
| 2012/0323144 A1 | 12/2012 | Coston et al. |
| 2012/0323502 A1 | 12/2012 | Tanoura et al. |
| 2013/0066166 A1 | 3/2013 | Burnett et al. |
| 2013/0109927 A1 | 5/2013 | Menzel |
| 2013/0109928 A1 | 5/2013 | Menzel |
| 2013/0131610 A1 | 5/2013 | Dewaele et al. |
| 2013/0218106 A1 | 8/2013 | Coston et al. |
| 2013/0245498 A1 | 9/2013 | Delaney et al. |

(56) References Cited

U.S. PATENT DOCUMENTS

| | | |
|---|---|---|
| 2013/0267871 A1 | 10/2013 | Delaney et al. |
| 2014/0039348 A1 | 2/2014 | Bullington et al. |
| 2014/0155781 A1 | 6/2014 | Bullington et al. |
| 2014/0155782 A1 | 6/2014 | Bullington et al. |
| 2014/0159921 A1 | 6/2014 | Qualey et al. |
| 2014/0207085 A1 | 7/2014 | Brandt et al. |
| 2014/0243635 A1 | 8/2014 | Arefieg |
| 2014/0335490 A1 | 11/2014 | Baarman et al. |
| 2015/0120321 A1 | 4/2015 | David et al. |
| 2015/0343173 A1 | 12/2015 | Tobescu et al. |
| 2015/0359522 A1 | 12/2015 | Recht et al. |
| 2015/0362351 A1 | 12/2015 | Joshi et al. |
| 2016/0051176 A1 | 2/2016 | Ramos et al. |
| 2016/0183819 A1 | 6/2016 | Burnett et al. |
| 2017/0043089 A1 | 2/2017 | Handler |
| 2017/0100068 A1 | 4/2017 | Kostov |
| 2017/0113000 A1 | 4/2017 | Tobescu et al. |
| 2017/0136209 A1 | 5/2017 | Burnett et al. |
| 2017/0196478 A1 | 7/2017 | Hunter |
| 2017/0202698 A1 | 7/2017 | Zani et al. |
| 2017/0249445 A1 | 8/2017 | Devries et al. |
| 2017/0290540 A1 | 10/2017 | Franco |
| 2017/0291012 A1 | 10/2017 | Iglesias |
| 2017/0307423 A1 | 10/2017 | Pahwa et al. |
| 2018/0015251 A1 | 1/2018 | Lampotang et al. |
| 2018/0214297 A1* | 8/2018 | Hughett ............... A61B 5/7445 |
| 2018/0280236 A1 | 10/2018 | Ludin et al. |
| 2018/0344234 A1 | 12/2018 | McKinney et al. |
| 2019/0046102 A1 | 2/2019 | Kushnir et al. |
| 2019/0069829 A1 | 3/2019 | Bulut |
| 2019/0069830 A1 | 3/2019 | Holt et al. |
| 2019/0126006 A1 | 5/2019 | Rehm et al. |
| 2019/0201596 A1 | 7/2019 | Luxon et al. |
| 2019/0223844 A1 | 7/2019 | Aboagye et al. |
| 2019/0247236 A1 | 8/2019 | Sides et al. |
| 2019/0321588 A1 | 10/2019 | Burnett et al. |
| 2019/0328945 A1 | 10/2019 | Analytis et al. |
| 2019/0358387 A1 | 11/2019 | Elbadry et al. |
| 2019/0365308 A1 | 12/2019 | Laing et al. |
| 2019/0381223 A1 | 12/2019 | Culbert et al. |
| 2020/0022637 A1 | 1/2020 | Kurzrock et al. |
| 2020/0064172 A1 | 2/2020 | Tabaczewski et al. |
| 2020/0085378 A1 | 3/2020 | Burnett et al. |
| 2020/0268303 A1 | 8/2020 | Oliva |
| 2020/0289749 A1 | 9/2020 | Odashima et al. |
| 2020/0405524 A1 | 12/2020 | Gill |
| 2021/0077007 A1 | 3/2021 | Jouret et al. |
| 2021/0299353 A1 | 9/2021 | Mannu et al. |
| 2022/0018692 A1 | 1/2022 | Tourchak et al. |
| 2022/0026001 A1 | 1/2022 | Cheng et al. |
| 2022/0026261 A1 | 1/2022 | Funnell et al. |
| 2022/0192564 A1 | 6/2022 | Kriscovich et al. |
| 2022/0192565 A1 | 6/2022 | Cheng et al. |
| 2022/0192566 A1 | 6/2022 | Cheng et al. |
| 2022/0233120 A1 | 7/2022 | Beuret et al. |
| 2022/0296140 A1 | 9/2022 | Nguyen et al. |
| 2022/0386917 A1 | 12/2022 | Mann et al. |
| 2023/0022547 A1 | 1/2023 | Cho et al. |
| 2023/0025333 A1 | 1/2023 | Patel et al. |
| 2023/0028966 A1 | 1/2023 | Franano |
| 2023/0035669 A1 | 2/2023 | Raja et al. |
| 2023/0040915 A1 | 2/2023 | Compton et al. |
| 2023/0058553 A1 | 2/2023 | Fallows et al. |
| 2023/0060232 A1 | 3/2023 | Patel et al. |
| 2023/0084476 A1 | 3/2023 | Robichaud et al. |
| 2024/0042120 A1 | 2/2024 | Cheng et al. |
| 2024/0081708 A1 | 3/2024 | Kelly et al. |
| 2024/0108268 A1 | 4/2024 | Woodard et al. |
| 2024/0252783 A1 | 8/2024 | Waitkus et al. |
| 2024/0347162 A1 | 10/2024 | Meese et al. |
| 2024/0360938 A1 | 10/2024 | Cheng et al. |

FOREIGN PATENT DOCUMENTS

| | | |
|---|---|---|
| CN | 200951235 Y | 9/2007 |
| CN | 201492414 U | 6/2010 |
| CN | 102647939 A | 8/2012 |
| CN | 107952140 A | 4/2018 |
| CN | 109498013 A | 3/2019 |
| CN | 110859636 A | 3/2020 |
| CN | 112426156 A | 3/2021 |
| EP | 0342028 A2 | 11/1989 |
| ES | 2760470 T3 | 5/2020 |
| GB | 2576743 A | 3/2020 |
| JP | 849-75171 A | 7/1974 |
| JP | S54-147066 A | 11/1979 |
| JP | 858-190719 A | 11/1983 |
| JP | 860-219517 A | 11/1985 |
| JP | H02-057240 B2 | 12/1990 |
| JP | H08-271301 A | 10/1996 |
| JP | H10-104041 A | 4/1998 |
| JP | 2007-303982 A | 11/2007 |
| JP | 2008-524618 A | 7/2008 |
| JP | 2009-068959 A | 4/2009 |
| JP | 2010-121950 A | 6/2010 |
| JP | 2010-530978 A | 9/2010 |
| JP | 2012-105947 A | 6/2012 |
| JP | 2012-225790 A | 11/2012 |
| RU | 2615727 C2 | 4/2017 |
| WO | 1981003427 A1 | 12/1981 |
| WO | 2004045410 A1 | 6/2004 |
| WO | 2013013782 A2 | 1/2013 |
| WO | 20130178742 A1 | 12/2013 |
| WO | 2014/043650 A2 | 3/2014 |
| WO | 2014108690 A1 | 7/2014 |
| WO | 2014/135856 A1 | 9/2014 |
| WO | 2014/151068 A2 | 9/2014 |
| WO | 2014145971 A2 | 9/2014 |
| WO | 201511402 A1 | 1/2015 |
| WO | 2015/105916 A1 | 7/2015 |
| WO | 2015/127390 A1 | 8/2015 |
| WO | 2015191125 A1 | 12/2015 |
| WO | 2016177901 A1 | 11/2016 |
| WO | 2017/023794 A1 | 2/2017 |
| WO | 2018156624 A1 | 8/2018 |
| WO | 2019066357 A1 | 4/2019 |
| WO | 2019/226697 A1 | 11/2019 |
| WO | 2020033752 A1 | 2/2020 |
| WO | 2020154370 A1 | 7/2020 |
| WO | 2022108589 A1 | 5/2022 |
| WO | 2022182794 A1 | 9/2022 |
| WO | 2023022895 A1 | 2/2023 |
| WO | 2023027871 A1 | 3/2023 |
| WO | 2023076067 A1 | 5/2023 |

OTHER PUBLICATIONS

EP 23188337.2 filed May 21, 2019 Extended European Search Report dated Dec. 4, 2023.

PCT/US2019/033389 filed Nov. 26, 2020 Extended European Search Report dated Jun. 4, 2021.

PCT/US2022/039191 filed Aug. 2, 2022 International Search Report and Written Opinion dated Dec. 5, 2022.

PCT/US2022/039746 filed Aug. 8, 2022 International Search Report and Written Opinion dated Nov. 18, 2022.

U.S. Appl. No. 17/054,493, filed Nov. 10, 2020 Notice of Allowance dated Jan. 4, 2024.

U.S. Appl. No. 17/306,821, filed May 3, 2021 Notice of Allowance dated Apr. 23, 2024.

U.S. Appl. No. 17/373,546, filed Jul. 12, 2021 Notice of Allowance dated Mar. 7, 2024.

U.S. Appl. No. 17/373,546, filed Jul. 12, 2021 Notice of Allowance dated May 29, 2024.

U.S. Appl. No. 17/556,907, filed Dec. 20, 2021 Notice of Allowance dated Dec. 6, 2023.

U.S. Appl. No. 17/556,931, filed Dec. 20, 2021 Non-Final Office Action dated Mar. 27, 2024.

U.S. Appl. No. 17/556,931, filed Dec. 20, 2021 Restriction Requirement dated Feb. 22, 2024.

(56) References Cited

OTHER PUBLICATIONS

PCT/US2019/045787 filed Aug. 8, 2019 International Preliminary Report on Patentability dated Feb. 16, 2021.
PCT/US2019/045787 filed Aug. 8, 2019 International Search Report and Written Opinion dated Oct. 2, 2019.
U.S. Appl. No. 17/262,080, filed Jan. 21, 2021 Non-Final Office Action dated Apr. 6, 2023.
U.S. Appl. No. 17/373,535, filed Jul. 12, 2021 Notice of Allowance dated Feb. 23. 2023.
JS U.S. Appl. No. 17/556,907, filed Dec. 20, 2021 Restriction Requirement dated May 12, 2023.
Bard Medical, Criticore Disposables—Non I.C., 3 pages, www.bardmedical.com/products/patienl-moniloring-, ystems/criticore®-system/criticore®-disposables-non-ic/ Jan. 30, 2015.
Bard Medical, Criticore Infection Control Disposables, 3 pages, www.bardmedical.com/patienl-moniloring-, ystems/criticore®-system/criticore®-infection-control-disposables/ Jan. 30, 2015.
Bard Medical, Criticore Monitor, 11 pages, www.bardmedical.com/products/patient-monitoring-systems/criticore®-monitor/ Jan. 30, 2015.
Bard Medical, Urine Meiers, 3 pages, www.bardmedical.com/products/urological-drainage/urine-collection/urinemeters/Jan. 30, 2015.
Biometrix, Urimetrix, 4 pages, www.biometrixmedical.com/Products/56/Urimetrix%E2%84%A2 Oct. 29, 2014.
Observe Medical, sippi, 3 pages, www.observemedical.com/products.html Oct. 29, 2014.
PCT/US19/33389 filed May 21, 2019 International Search Report and Written Opinion dated Aug. 2, 2019.
PCT/US2016/044835 filed Jul. 20, 2016 International Search Report and Written Opinion dated Dec. 16, 2016.
U.S. Appl. No. 17/054,493, filed Nov. 10, 2020 Final Office Action dated May 31, 2022.
U.S. Appl. No. 15/748,107 filed Jan. 26, 2018 Final Office Action dated Dec. 23, 2020.
U.S. Appl. No. 15/748,107 filed Jan. 26, 2018 Final Office Action dated Feb. 7, 2022.
U.S. Appl. No. 15/748,107 filed Jan. 26, 2018 Non-Final Office Action dated Sep. 3, 2021.
U.S. Appl. No. 15/748,107 filed Jan. 26, 2018 Non-Final Office Action dated Sep. 4, 2020.
U.S. Appl. No. 17/054,493 filed Nov. 10, 2020 Non-Final Office Action dated Nov. 24, 2021.
DFree Personal—Consumer Product Brochure, 2019.
DFree Pro Brochure 2019.
Leonhäuser, D et al., "Evaluation of electrical impedance tomography for determination of urinary bladder vol. comparison with standard ultrasound methods in healthy volunteers." - BioMed Engr On-line; 17:95; 2018.
Li, R., et al., "Design of a Noninvasive Bladder Urinary vol. Monitoring System Based on Bio-Impedance."—Engineering; vol. 5; pp. 321-325; 2013.
PCT/US20/61367 filed Nov. 19, 2020 International Search Report and Written Opinion dated Feb. 22, 2021.
PCT/US2022/017574 filed Feb. 23, 2022 Internation Search Report and Written Opinion dated Jun. 8, 2022.
Reichmuth, M., et al., "A Non-invasive Wearable Bioimpedance System to Wirelessly Monitor Bladder Filling."—Dep. of Health Sciences and Technology—Department of Information Technology and Electrical Engineering ETH Zurich, Zurich, Switzerland—Conference Paper; Mar. 2020.
Schlebusch, T. et al., "Bladder vol. estimation from electrical impedance tomography" Physiological Measurement, Institute of Physics, Bristol, GB. vol. 35 no. 9 Aug. 20, 2014. (Aug. 20, 2014).
SECA product catalog, https://US.secashop.com/products/seca-mbca/seca-mbca-514/5141321139, last accessed Sep. 11, 2020.
U.S. Appl. No. 17/054,493, filed Nov. 10, 2020 Final Office Action dated Oct. 4, 2023.
U.S. Appl. No. 17/262,080, filed Jan. 21, 2021 Final Office Action dated Sep. 11, 2023.
U.S. Appl. No. 17/262,080, filed Jan. 21, 2021 Notice of Allowance dated Oct. 13, 2023.
U.S. Appl. No. 17/306,821, filed May 3, 2021 Advisory Action dated Oct. 3, 2023.
U.S. Appl. No. 17/306,821, filed May 3, 2021 Final Office Action dated Jul. 19, 2023.
U.S. Appl. No. 17/373,546, filed Jul. 12, 2021 Non-Final Office Action dated Nov. 1, 2023.
U.S. Appl. No. 17/556,907, filed Dec. 20, 2021 Non-Final Office Action dated Aug. 17, 2023.
U.S. Appl. No. 15/748,107 filed Jan. 26, 2018 Notice of Allowance dated Dec. 12, 2022.
U.S. Appl. No. 17/054,493, filed Nov. 10, 2020 Non-Final Office Action dated Jan. 27, 2023.
US 17/3026,821 filed May 3, 2021 Non-Final Office Action dated Jan. 10, 2023.
U.S. Appl. No. 17/373,535, filed Jul. 12, 2021 Non-Final Office Action dated November 9. 2022.
"Urocare Reusable Night Drain Bottle—Urinary Collection System" Aug. 13, 2020, HealthProductsForYou.com, <https://www.healthproductsforyou.com/p-urocare-reusable-night-drain-bottle-urinary-collection-system.html> retrieved from Archive.org (Year: 2020).
U.S. Appl. No. 17/552,250, filed Dec. 15, 2021 Non-Final Office Action dated Sep. 19, 2024.
U.S. Appl. No. 17/556,931, filed Dec. 20, 2021 Final Office Action dated Oct. 1, 2024.

\* cited by examiner

AUTOMATED WEIGHT BASED FLUID OUTPUT MONITORING SYSTEM

PRIORITY

This application claims the benefit of priority to U.S. Provisional Application No. 63/130,301, filed Dec. 23, 2020, which is incorporated by reference in its entirety into this application.

BACKGROUND

Accurately measuring fluid output is important in monitoring patient health and for accurate diagnoses. Automatic fluid output measuring systems have been developed to detect changes in fluid output volume by detecting a change in weight of a fluid collection device. As such, the interface mechanisms configured to engage the fluid collection system with the automatic fluid flow require a secure fit to ensure the downward forces, or changes thereof, are accurately transferred to the automatic fluid flow system. However, such systems can require complicated attachment systems to both ensure a secure fit and compensate for off-axis loading, where the weight of the collection bag is at an angle to a transverse axis. Disclosed herein are automated weight based fluid output monitoring systems and associated methods of use that address the foregoing.

SUMMARY

Disclosed herein is an automated fluid monitoring system including, a stand including a socket extending along a transverse axis, a hanger having a securement ball defining a semi-spherical shape and including a hook extending therefrom along a first axis, the hook coupled with a fluid collection bag, the securement ball configured to rotatably engage the socket, and a sensor array disposed on a surface of the securement ball and configured to detect a change in pressure between the hanger and the stand, and detect an angle of pressure along the first axis, relative to the transverse axis.

In some embodiments, the sensor array includes one or more pressure sensors disposed on the semi-spherical surface of the securement ball.

In some embodiments, the socket is configured to engage the securement ball to prevent linear movement along the longitudinal and lateral axes and allow the first axis of the hook to pivot relative to the transverse axis.

In some embodiments, the socket defines a semi-spherical concave shape.

In some embodiments, the automated fluid monitoring system further includes a console including one or more processors, an energy source, a data store, a calibration logic, a pressure mapping logic and a fluid output logic.

In some embodiments, the console is disposed within the hanger and communicatively coupled with one of the stand, a network, an external computing device, or an electronic health record system.

In some embodiments, the console is disposed within the stand and is communicatively coupled with the sensor array by way of a connector wire or a port disposed on the hanger.

In some embodiments, the console is disposed remotely from both the hanger and the stand as a stand-alone device and is wirelessly communicatively coupled with the sensor array.

In some embodiments, the fluid output logic is configured to receive a signal from the sensor array and determine a fluid volume within the fluid collection bag, or a change in fluid volume within the fluid collection bag over time.

In some embodiments, the pressure mapping logic is configured to receive a signal from the sensor array and determine an angle of the first axis relative to the transverse axis.

In some embodiments, the calibration logic is configured to receive a signal from the sensor array and calibrate one or more of the sensor array, the fluid output logic and the pressure mapping logic.

In some embodiments, the fluid collection bag is in fluid communication with a catheter and configured to drain a fluid from a bladder of a patient.

In some embodiments, the hanger further includes a stabilizing handle configured to engage one of a medical bed, a door, or an intravenous pole.

In some embodiments, the hook is selectively detachable from the hanger.

Also disclosed is a method of measuring a fluid output from a patient including, coupling a spherical surface of a securement ball of a hanger with a concave socket of a stand, the socket defining a transverse axis and allowing the hangar to pivot about the transverse axis relative to the stand, coupling a fluid collection bag with a hook of the hanger, the hook extending along a first axis, applying a force to the hanger along the first axis, detecting a change in pressure between the securement ball and the socket, determining a volume of fluid within the fluid collection bag, and determining an angle of the first axis relative to the transverse axis.

In some embodiments, the spherical surface includes a sensor array including one or more pressure sensors.

In some embodiments, the securement ball engages the socket to prevent linear movement of the hanger along a longitudinal axis or a lateral axis.

In some embodiments, determining a volume of fluid or determining an angle of the first axis is performed by a console disposed within the hanger and including one or more of a processor, an energy source, a data store, a calibration logic, a pressure mapping logic and a fluid output logic.

In some embodiments, determining a volume of fluid or determining an angle of the first axis is performed by a console disposed within the stand and communicatively coupled with the hanger, the console including one or more of a processor, an energy source, a data store, a calibration logic, a pressure mapping logic and a fluid output logic.

In some embodiments, the method further includes determining a change in fluid volume within the fluid collection bag over time using a fluid output logic.

In some embodiments, applying a force to the hanger along the first axis includes draining a fluid from a patient into the fluid collection bag, the fluid collection bag in fluid communicating with a Foley catheter.

These and other features of the concepts provided herein will become more apparent to those of skill in the art in view of the accompanying drawings and following description, which describe particular embodiments of such concepts in greater detail.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Figure 1:
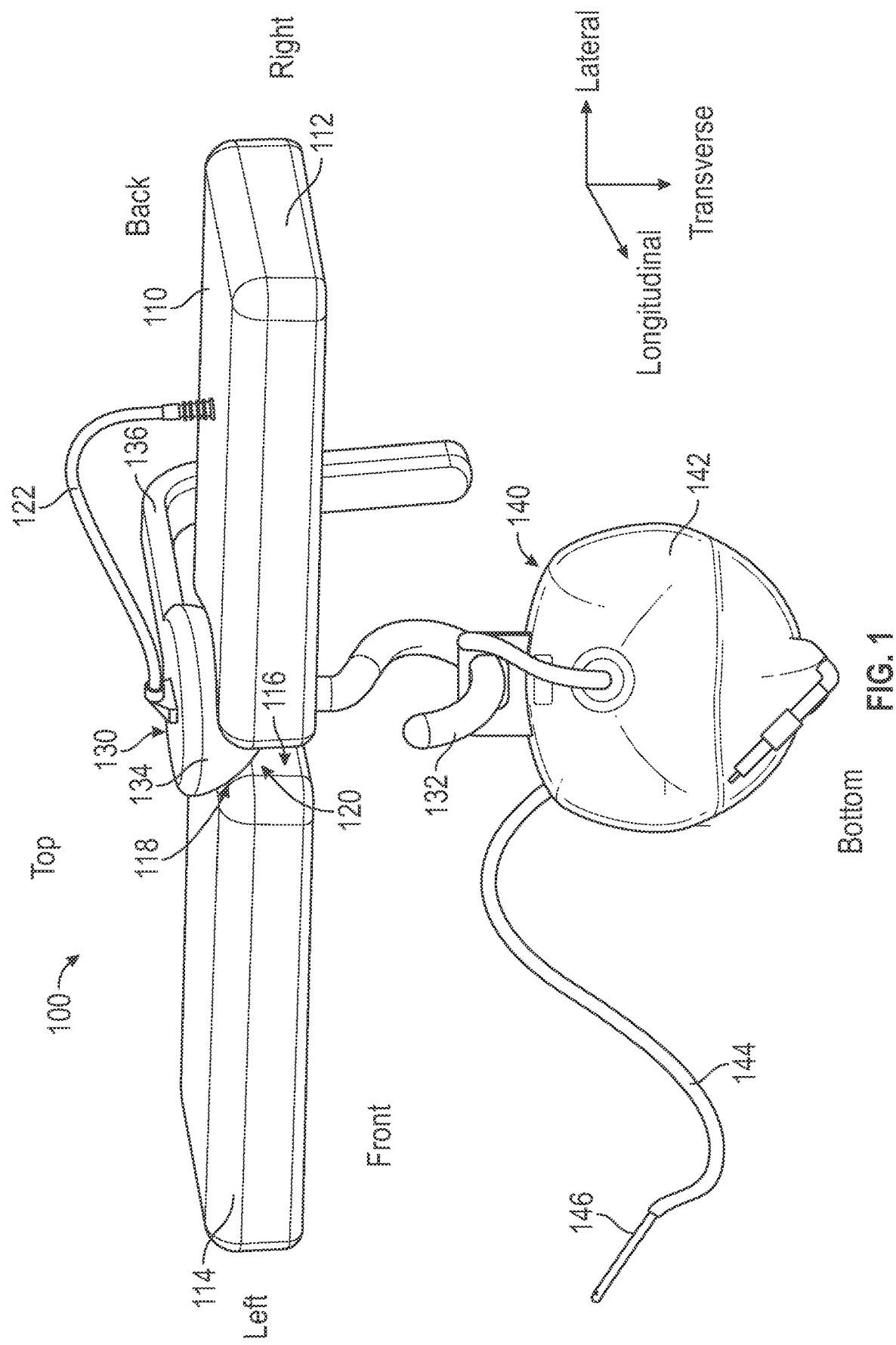
FIG. 1 illustrates a perspective view of a fluid monitoring system, in accordance with embodiments disclosed herein.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

In the following description, the terms "or" and "and/or" as used herein are to be interpreted as inclusive or meaning any one or any combination. As an example, "A, B or C" or "A, B and/or C" mean "any of the following, A, B, C, A and B, A and C, B and C, A, B and C." An exception to this definition will occur only when a combination of elements, components, functions, steps or acts are in some way inherently mutually exclusive.

In the following description, certain terminology is used to describe aspects of the invention. For example, in certain situations, the term "logic" is representative of hardware, firmware or software that is configured to perform one or more functions. As hardware, logic may include circuitry having data processing or storage functionality. Examples of such circuitry may include, but are not limited or restricted to a hardware processor (e.g., microprocessor with one or more processor cores, a digital signal processor, a programmable gate array, a microcontroller, an application specific integrated circuit "ASIC," etc.), a semiconductor memory, or combinatorial elements.

Alternatively, logic may be software, such as executable code in the form of an executable application, an Application Programming Interface (API), a subroutine, a function, a procedure, an applet, a servlet, a routine, source code, object code, a shared library/dynamic load library, or one or more instructions. The software may be stored in any type of a suitable non-transitory storage medium, or transitory storage medium (e.g., electrical, optical, acoustical or other form of propagated signals such as carrier waves, infrared signals, or digital signals). Examples of non-transitory storage medium may include, but are not limited or restricted to a programmable circuit; semiconductor memory; non-persistent storage such as volatile memory (e.g., any type of random access memory "RAM"); or persistent storage such as non-volatile memory (e.g., read-only memory "ROM," power-backed RAM, flash memory, phase-change memory, etc.), a solid-state drive, hard disk drive, an optical disc drive, or a portable memory device. As firmware, the executable code may be stored in persistent storage.

The term "computing device" should be construed as electronics with the data processing capability and/or a capability of connecting to any type of network, such as a public network (e.g., Internet), a private network (e.g., a wireless data telecommunication network, a local area network "LAN", etc.), or a combination of networks. Examples of a computing device may include, but are not limited or restricted to, the following: a server, an endpoint device (e.g., a laptop, a smartphone, a tablet, a "wearable" device such as a smart watch, augmented or virtual reality viewer, or the like, a desktop computer, a netbook, a medical device, or any general-purpose or special-purpose, user-controlled electronic device), a mainframe, internet server, a router; or the like.

A "message" generally refers to information transmitted in one or more electrical signals that collectively represent electrically stored data in a prescribed format. Each message may be in the form of one or more packets, frames, HTTP-based transmissions, or any other series of bits having the prescribed format.

The term "computerized" generally represents that any corresponding operations are conducted by hardware in combination with software and/or firmware.

Labels such as "left," "right," "upper", "lower," "top," "bottom," "front," "back," and the like are used for convenience and are not intended to imply, for example, any particular fixed location, orientation, or direction. Instead, such labels are used to reflect, for example, relative location, orientation, or directions. To assist in the description of embodiments described herein, the "top," "bottom," "left," "right," "front" and "back" directions are in reference to the orientation of the device as shown in FIG. 1. To assist in the description of embodiments described herein, as shown in FIG. 1, a longitudinal axis extends substantially parallel to an axis extending between a front side and a back side of the device. A lateral axis extends normal to the longitudinal axis, between a left side and a right side, and a transverse axis extends normal to both the longitudinal and lateral axes between a top side and a bottom side.

Unless defined otherwise, all technical and scientific terms used herein have the same meaning as commonly understood by those of ordinary skill in the art.

FIG. 1 illustrates a perspective view of an automated weight-based fluid output monitoring system ("fluid monitoring system," or "system") 100, in accordance with some embodiments. In some embodiments, the system 100 can generally include a stand 110, a fluid collecting bag hanger ("hanger") 130, and a fluid collection system 140 having a fluid collection bag 142 or similar container that is in fluid communication with a drainage tube 144 and a catheter 146.

In an embodiment, the hanger 130 can generally include a securement ball 134 defining a spherical or semi-spherical surface, and can have a hook 132 extending therefrom along a transverse axis. Optionally, the hanger 130 can include a stabilization handle ("handle") 136. In an embodiment, the hook 132 can releasably engage the fluid collecting bag 142 of a fluid collection system 140, wherein the fluid collecting bag 142 is suspended from the hook 132. In an embodiment, the hook 132 can be formed integrally with the collection bag 142. The hook 132 may extend transversely from the securement ball 134, as illustrated in FIG. 1, however in an embodiment, the hook 132 can also extend longitudinally, laterally, or at an angle thereto, without limitation.

In some embodiments, the hanger 130 may also include a stabilizing handle 136, extending from the securement ball 134 and configured to engage a hospital bed, a door, an intravenous pole, or similar structure to stabilize the system 100, or components thereof. In an embodiment, the stabilizing handle 136 may be configured to detachably couple to a hospital bed, a door, an intravenous pole or the like. Optionally, the handle 136 can be configured to be grasped by a user and facilitate manipulation of the hanger 130 and collection bag 142 coupled thereto.

In some embodiments, the system 100 can further include a stand 110 configured to engage and support the hanger 130 allowing the fluid collection bag 142 to suspend therefrom. In an embodiment, the stand 110 can include a concave socket ("socket") 118 configured to engage a surface of the securement ball 134. In an embodiment, the securement ball 134 can engage the socket 118 and can prevent any longitudinal, lateral, or downward transverse movement of the securement ball 134 relative to the stand 110. In an embodiment, the socket 118 can allow the securement ball 134 to rotate or pivot within the socket 118, allowing an axis of the hanger 130 to pivot relative to the stand 110. As shown, the socket 118 can define a spherical concave shape having a radius of curvature similar to that of the spherical portions of the securement ball 134.

In an embodiment, the socket 118 can also include one or more notches, forks, holes, slots, or the like, configured to engage a portion of the securement ball 134 and allow the collection bag 142 to be suspended from the hook 132. In some embodiments, the stand 110 can include a right arm 112 and a left arm 114 bisected by a channel 116, extending from the front to the back of the stand 110. In some embodiments, the stand 110 may be coupled to a medical bed, a door, an intravenous pole or the like. In an embodiment, a surface of the right arm 112, a surface of the left arm 114, the channel 116, or combinations thereof can co-operate to define the socket 118. In an embodiment, the socket 118 may be configured to receive therein the securement ball 134 and contact at least a portion of the securement ball 134. In an embodiment, the socket 118 may be a recessed hemisphere, a cradle, a cup, a recessed half cylinder or the like. In some embodiments, the socket 118 may be shaped to correspond to the shape of the securement ball 134. Where the securement ball 134 contacts the socket 118 will be referred to herein as the securement ball/socket interface 120. In some embodiments, the channel 116 may be configured to allow the hook 132 to extend therethrough. The channel 116 may allow a user to pivot, tilt, or move the hook 132 forwards or backwards, as described in more detail herein. The socket 118 including the channel 116 may be configured to secure the securement ball 134, mitigating lateral or longitudinal movement.

In an embodiment, the hanger 130 can be communicatively coupled with the stand 110 be either wired or wireless communication systems. As shown, the hanger 130 can include a wired connector 122 to couple the hanger 130 with the stand 110 by wired communication. In an embodiment, the hangar 130 can be wirelessly coupled with the stand 110 using Bluetooth, WiFi, Global System for Mobiles ("GSM"), Near Field Communications ("NFC"), combinations thereof, or the like. In an embodiment, the connector 122 can releasably engage the stand 110. In an embodiment, the connector 122 can be formed integrally with the hanger 130. In an embodiment, the connector 122 can be releasably coupled with the hanger 130.

In some embodiments, the fluid collecting bag 142 may be in fluid communication with a catheter 146 or similar medical device configured to drain a fluid from a cavity of a patient. In an embodiment, the catheter may be an internal catheter or an external catheter. Exemplary catheters can include external urinary catheters, internal urinary catheters, Foley catheters, securement balloon catheters, peritoneal catheters, or the like. Exemplary fluids collected can include urine, blood, peritoneal fluid, interstitial fluid, or the like. In an embodiment, the catheter can be a Foley catheter configured to drain a fluid (e.g. urine), from a bladder of a patient.

Figure 2:
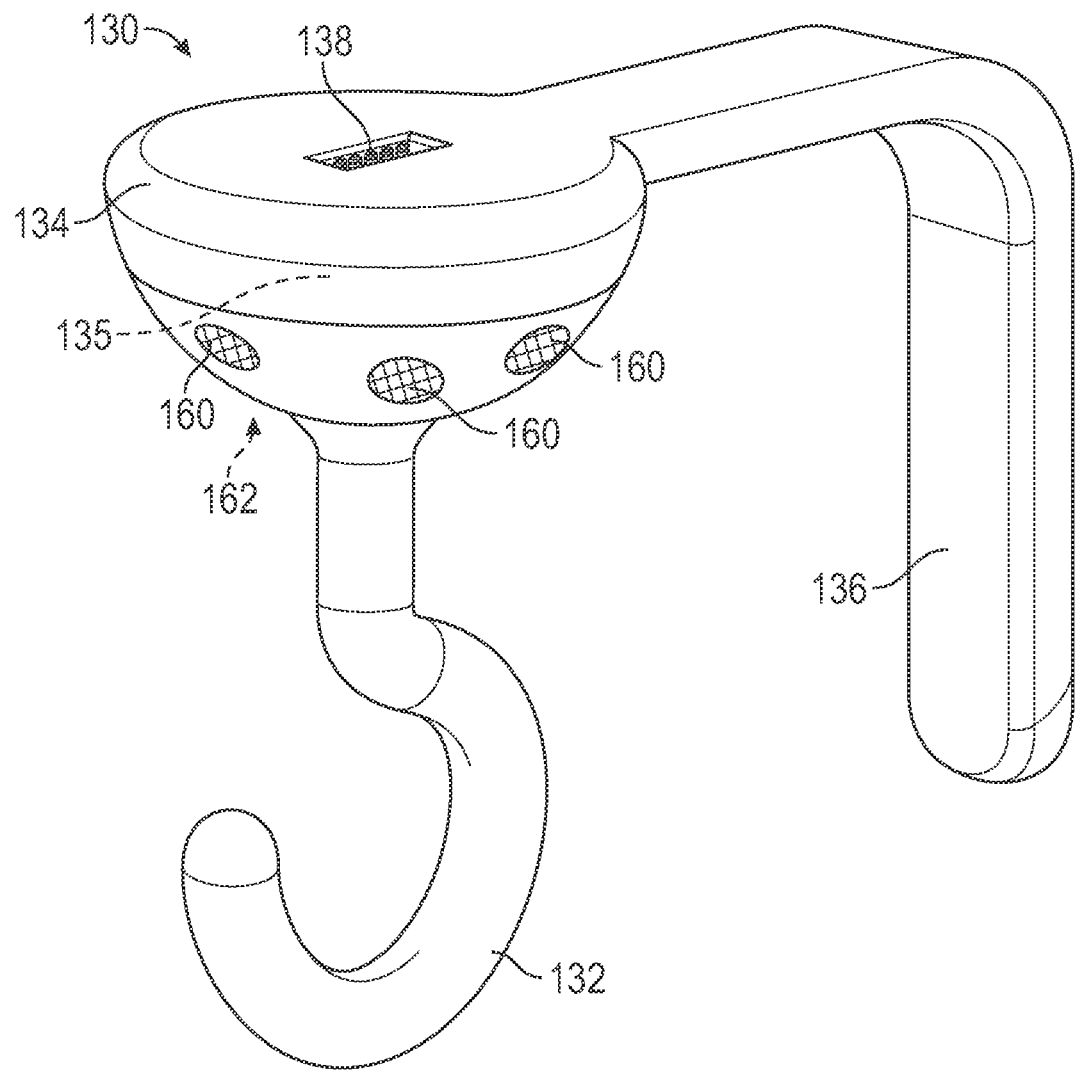
FIG. 2 illustrates a perspective view of a fluid bag hanger of a fluid monitoring system, in accordance with embodiments disclosed herein.
Figure 2:
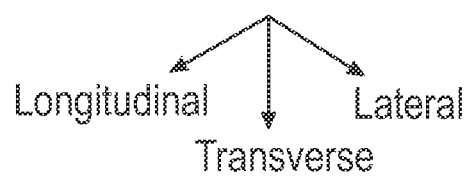

FIG. 2 illustrates further details of the hanger 130. In some embodiments, the fluid collecting bag hanger 130 includes the securement ball 134 and the hook 132. In some embodiments, the stabilizing handle 136 includes a first portion extending longitudinally from the securement ball 134 and a second portion extending transversely therefrom. It will be appreciated that various shapes and configurations of stabilization handle 136 are contemplated to fall within the scope of the present invention. In some embodiments, the securement ball 134 may be shaped in a sphere, a hemisphere, a regular or irregular ellipsoidal or ovoid shape, "egg" shape, a spherical polyhedron, a pentagonal prism, hexagonal prism, octagonal polyhedron, or the like. In an embodiment, as illustrated in FIG. 2, the securement ball 134 may be substantially shaped into a hemisphere.

In some embodiments, the securement ball 134 can define an interior cavity 135, configured to receive one or more of a sensor array 162, console 170, or components thereof, as described in more detail herein. In an embodiment, the sensor array 162 can include one or more sensors 160, e.g. a pressure sensor, gyroscopic sensors, accelerometers, or the like, disposed within the securement ball 134, e.g. within the interior cavity 135 defined by the securement ball 134, or disposed on a surface of the securement ball 134. In some embodiments, the one or more sensors 160, e.g. pressure sensors, may be configured in a sensor array 162 that can detect a change in weight of the fluid collecting bag 142, and therefore a change in volume of fluid disposed within the fluid collecting bag 142 as the fluid collecting bag 142 exerts a downward force on hook 132. In an embodiment, one or more sensors 160 can be disposed within the securement ball cavity 135. In an embodiment, one or more sensors 160 can be disposed on a surface of the securement ball 134, for example, on a surface of the securement ball 134 that engages the socket 118, i.e. the interface 120.

In an embodiment, a surface of the securement ball 134, e.g. a top surface, can include a port 138 configured to releasably engage the connector wire 122 and communicatively couple the hanger 130 with the stand 110, as described in more detail herein. In an embodiment, the port 138 may be configured transmit data or power to/from the hanger 130.

In an embodiment, the hook 132 can be fixedly coupled to the securement ball 134 so as to prevent any relative movement therebetween. In an embodiment, the hook 132 can be rotatably coupled to the securement ball 134 to allow the hook 132 to pivot relative to the securement ball 134 through one or more axes. In an embodiment, the hook 132 can be slidably engaged with the securement ball 134, for example, along a transverse axis. In an embodiment, a sensor 160 can be disposed between the hook 132 and securement ball 134 and can determine a change in pressure between the hook 132 and the securement ball 134.

In an embodiment, the hook 132 may be selectively detachable from the hanger 130 and may be disposable. In an embodiment, the fluid collecting bag hanger 130 may be disposable or reusable. In an embodiment, the hanger 130 may be configured to allow the sensor array 162 to be removed from the cavity 135, secured for sterilization and cleaning of the hanger 130 and replaced after sterilization and cleaning of the hanger 130. Advantageously, a disposable fluid collecting bag hanger 130 mitigates the effect of "long term drift" in the calibration of a hanger 130. As used herein, "long term drift" is the amount of change in the calibration between an actual measurement value and a detected measurement value. For example a change between the detected weight of fluid relative to an actual weight of fluid within the collection bag 142.

Figure 3A:
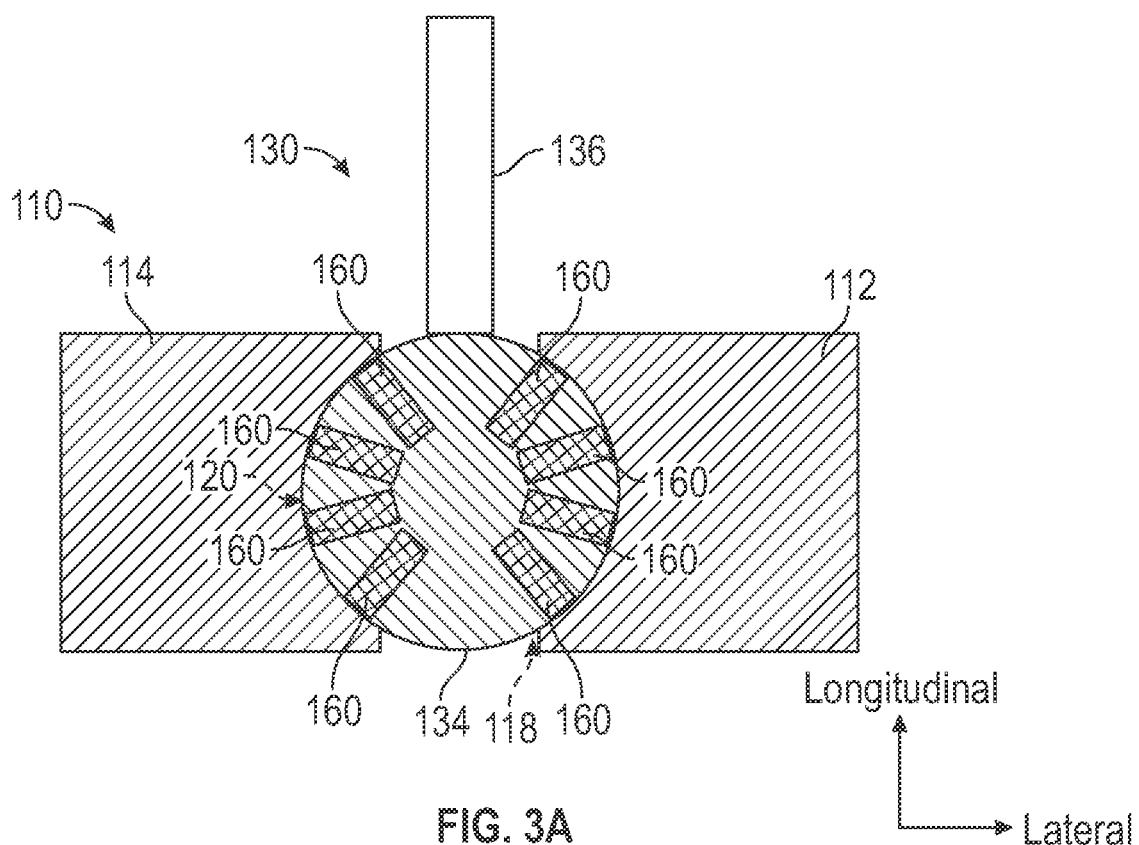
FIGS. 3A-3B illustrate plan views of various configurations of pressure mapping arrays for a fluid monitoring system, in accordance with embodiments disclosed herein.
Figure 3B:
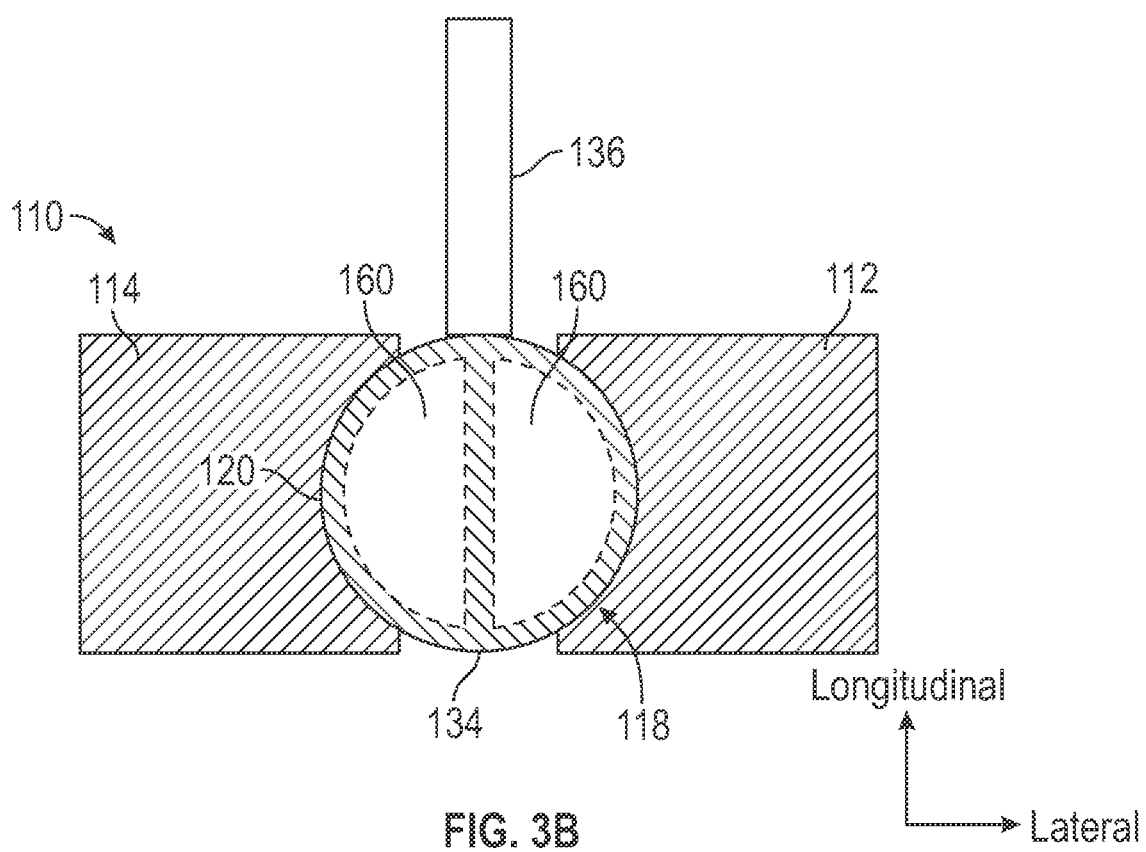

FIGS. 3A-3B illustrate various configurations one or more sensors 160 of the sensor array 162 on the hanger 130, in accordance with some embodiments. In some embodiments, the one or more sensors 160 may be arranged regularly or irregularly over a surface of the securement ball 134. In an embodiment, the sensors 160 can be arranged linearly, diagonally, hexagonally or "honey comb" pattern, or in various configurations of circle packing over a surface of the securement ball 134, without limitation. In an embodiment, the sensors 160 disposed on a surface of the securement ball 134 can be pressure sensors configured to determine a pressure between a surface of the securement ball 134 and a surface of the stand 110, e.g. the socket 118. In an embodiment, the sensor array 162 can include a gyroscopic sensor 160, an accelerometer 160, or similar sensor 160, disposed within a cavity 135 of the securement ball 134 and configured to detect a location, orientation, or change in relative speed of the securement ball 134 relative to the stand 110.

In some embodiments, the one or more sensors 160 may be arranged to cover at least a portion the securement ball/socket interface 120. In some embodiments, as illustrated in FIG. 3B, the sensor array 162 may include two quarter-spherical sensors 160, each configured to cover half of the semi-spherical securement ball-socket interface 120. It will be appreciated, however, that other numbers, arrangements or configurations of the one or more sensors 160 of the sensor array 162 are contemplated to fall within the scope of the present invention.

In use, a change in fluid volume within the fluid collecting bag 142, and thereby a change in weight of the fluid collecting bag 142, causes a change in pressure between a surface of the securement ball 134 and a surface of the socket 118, i.e. at the interface 120. This change in pressure at the interface 120 can be detected by one or more sensors 160 of the sensor array 162. In an embodiment, the change in weight of the collection bag 142 causes a change in location, orientation, or movement of the securement ball 134 relative to the stand 110 which can be detected by one or more gyroscopic or accelerometer sensors 160 of the sensor array 162.

In an embodiment, the change in pressure can be detected by the one or more sensors 160 in the sensor array 162 and communicated to a console 170 for further analysis. In an embodiment, the change in pressure can be substantially along a transverse axis, termed "on-axis." However, it will be appreciated that the change in pressure can exerted along an axis extending at an angle relative to the transverse axis of the hanger 130, termed "off-axis." Advantageously, with one or both of the on-axis loading or the off-axis loading, the ball-and-socket interface 120 can provide an even pressure over a surface of the interface 120 and can provide an even application of pressure to the sensor array 162, mitigating errors in fluid volume detection. In an embodiment, the sensory array 162 disposed over the spherical surface of the securement ball 134 can detect a force, or change in pressure, and an angle of the force, relative to the transverse axis of the stand 110. This information can be detected and transmitted to the console 170. In an embodiment, the sensors 160 of the sensor array 162 may be communicatively coupled with a console 170 by way of the port 138 and connector 122. As such one or more signals from the sensor array 162 can be communicated to a console 170 to store and analyze the information.

Figure 3C:
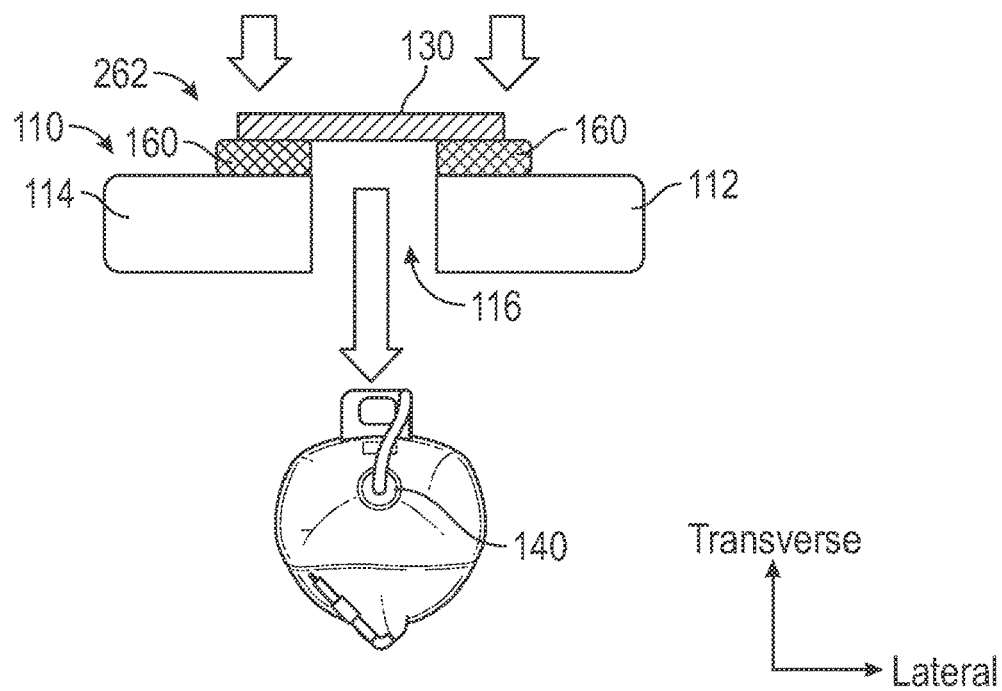
FIGS. 3C-3D illustrate a schematic view of a weight based fluid measuring system with off-axis loading, in accordance with embodiments disclosed herein.
Figure 3D:
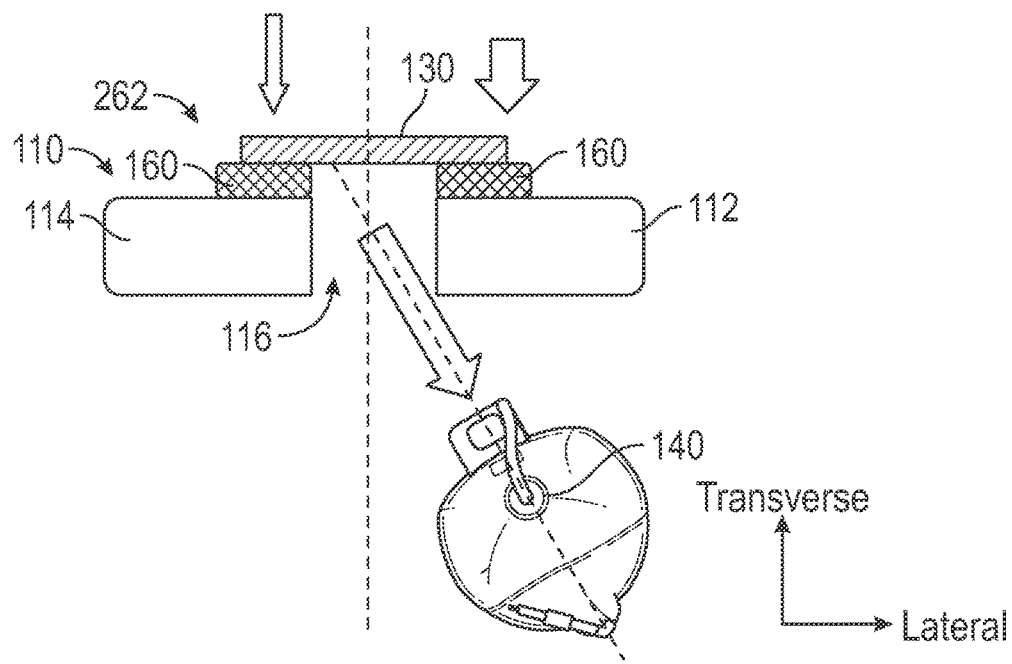

Advantageously, the sensor array 162 disposed over a spherically shaped interface 120 can mitigate errors incurred from off-axis loading. The spherically shaped sensor array 162 can always provide a sensor 160 aligned with the direction of force from the collection bag 142, even if the collection bag 142 is not aligned with the transverse axis of the stand. For example, FIGS. 3C-3D show a linear sensor array 262 having one or more sensors 160, as described herein, aligned perpendicular to a transverse axis of the stand 110. Where a force is applied from the collection bag 142 along the transverse axis, i.e. "on-axis," the pressure is applied evenly to the sensors 160 of the sensor array 162 and the weight of the collection bag 142 can be accurately determined. However, as shown in FIG. 3D, often the collection bag 142 applies a force that is "off-axis" from the transverse axis, for example, during transport, or movement of the system 100. As such, as shown in FIG. 3D, the force of the collection bag 142 is applied unevenly across the linear sensor array 162, leading to differences in pressure readings from the different sensors 160 and errors in fluid volume measurements. Often such systems require additional gyroscopes, accelerometers, or similar tilt sensors to detect off-axis loading and adjust the fluid volume readings by averaging, or by using various statistical estimation algorithms.

Figure 3E:
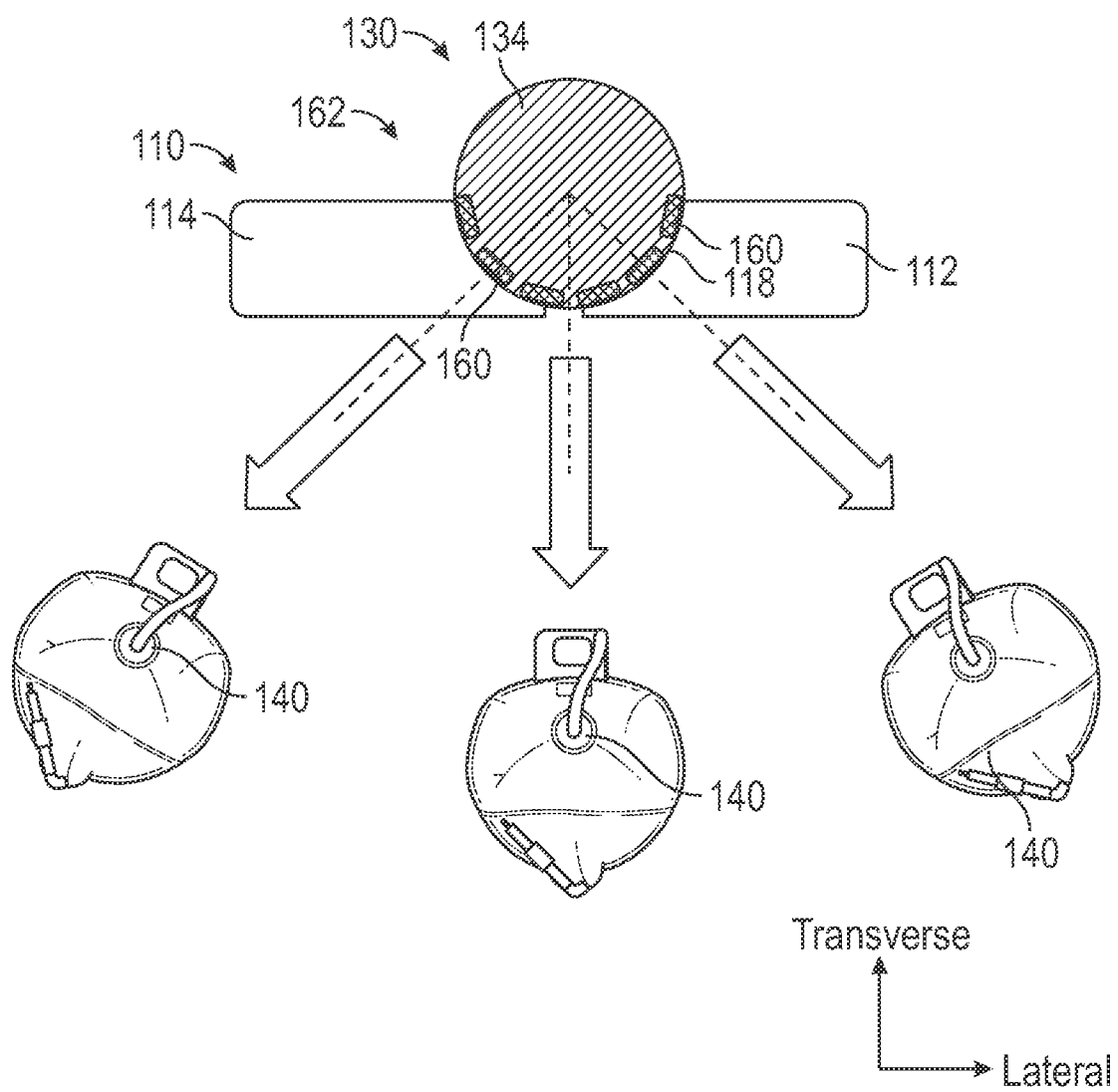
FIG. 3E illustrates a schematic view of a weight based fluid measuring system with off-axis loading, in accordance with embodiments disclosed herein.

By contrast, as shown in FIG. 3E, the spherical sensor array 162 of embodiments disclosed herein always provides a sensor 160 of the sensor array 162 that is aligned with the direction of force from the collection bag 142, no matter whether the force is applied parallel with the transverse axis of the stand 110 (i.e. on-axis), or at an angle relative to the transverse axis (i.e. off-axis). As such, the system 100 can provide accurate fluid volume readings at all times, and does not require additional gyroscope, accelerometers, or tilt sensors which can be susceptible to complex statistical algorithms to compensate for potential errors.

Figure 3F:
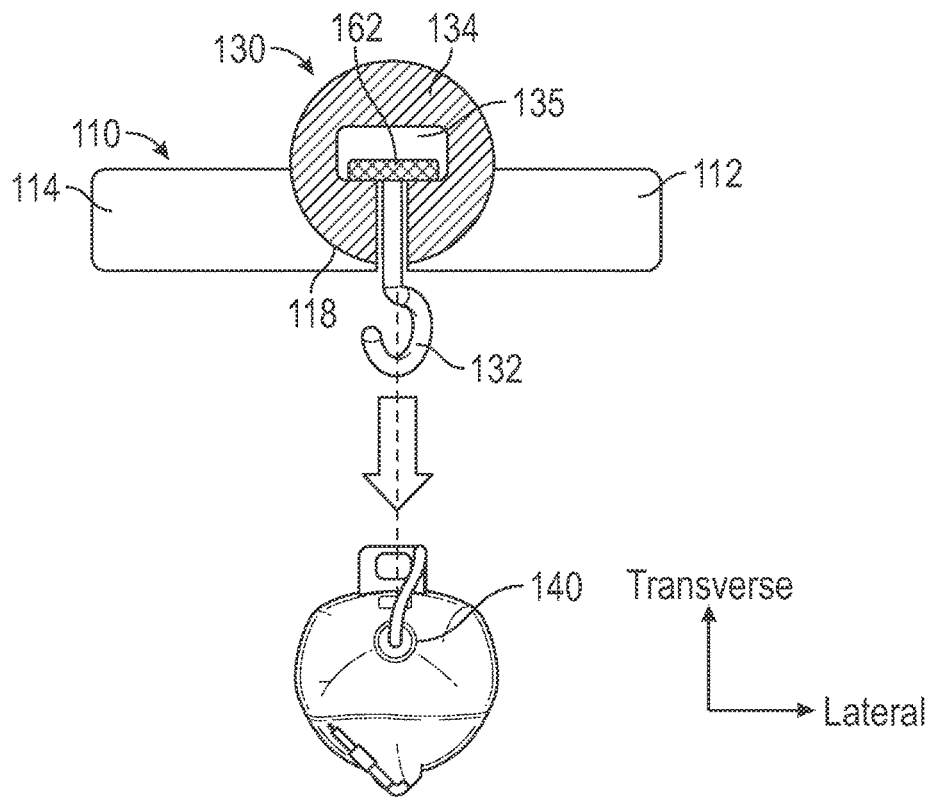
FIGS. 3F-3G illustrates a schematic view of a weight based fluid measuring system with off-axis loading, in accordance with embodiments disclosed herein.
Figure 3G:
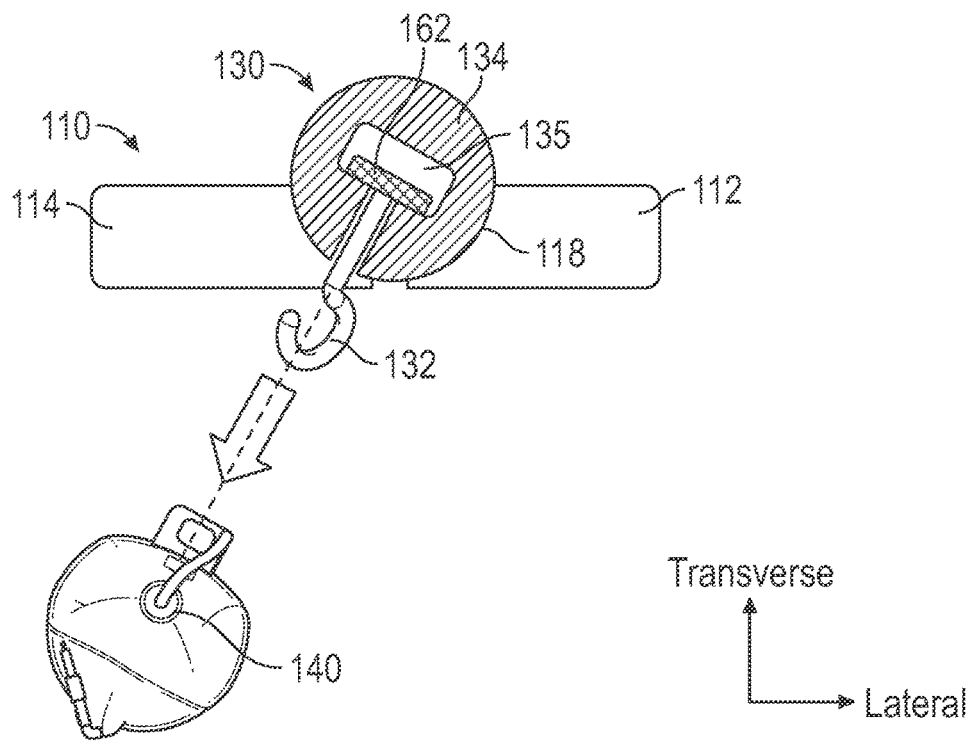

In an embodiment, as shown in FIGS. 3F-3G, the hook 132 can be slidably engaged with the securement ball 134 along an axis of the hook 132. The sensor array 162 can be aligned with the axis of the hook 132. As such any force applied to the hook 132 can be applied evenly to the sensor array 162 and an accurate weight, and therefore fluid volume, can be determined. In an embodiment, the securement ball 134 can pivot within the socket 118 through the longitudinal or lateral axes. As such, where the collection bag 142 is off-axis relative to a transverse axis of the stand 110, the axis of the hook and the sensor array 162 within the securement ball 134 can remain on-axis with the direction of force from the collection bag 142.

In an embodiment, the hanger 130 can be used as a stand-alone device to automatically measure fluid output and does not require specialized stands having specialized connection interfaces, moving parts, or the like. For example, the stand 110 as shown provides a concave socket 118 to receive the securement ball 134. However, the hanger 130 can also engage any stand having a hole, fork, slot, or similar structure configured to receive the securement ball 134 therein, and prevent axial movement of the hanger 130 relative to the stand, but allow the rotational movement. The hanger 130 can continue to operate measuring changes in fluid volume without being affected by off-axis loading. This can increase versatility of the hangar 130 and increase the mobility of the system 100.

Figure 4:
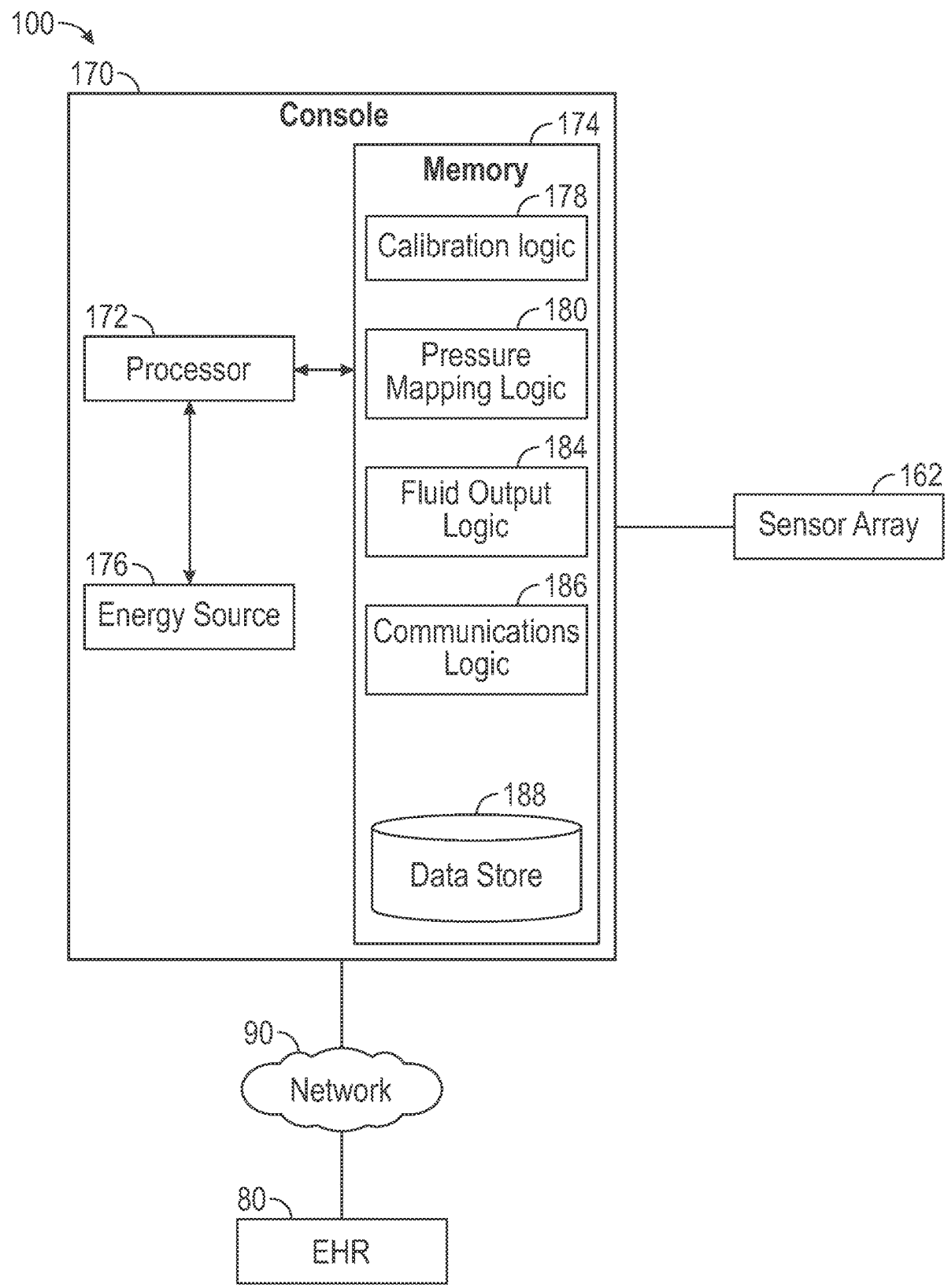
FIG. 4 illustrate a schematic view of a fluid monitoring system, in accordance with embodiments disclosed herein.

FIG. 4 illustrates a schematic view of a console 170 and associated components that is communicatively coupled with the sensor array 162. In an embodiment, the console 170, or one or more components thereof can be disposed within the cavity 135 of the hanger 130. In an embodiment, the console 170, or one or more components thereof can be disposed within the stand 110 and communicatively coupled with the sensor array 162 by either wired or wireless communication, for example wired communication by way of the connector wire 122 and port 138. In an embodiment, the console 170, or one or more components thereof can be disposed remotely from one or both of the hanger 130 and the stand 110 and communicatively coupled with the sensor array 162 by either wired or wireless communication, as described herein. These and other combinations or arrangements of the console 170, components thereof, hanger 130, and/or stand 110 are contemplated to fall within the scope of the present invention.

In an embodiment, the console 170 can be communicatively coupled, by either wired or wireless communication with one or more external computing devices 80 either directly or indirectly through a centralized or decentralized network 90. For example, the console 170 can be coupled with a hospital network 90, intranet, internet, "cloud" based network, or electronic health record system (EHR) 80, or combinations thereof.

In an embodiment, the console 170 can generally include one or more processors 172, non-transitory storage medium ("memory") 174, an energy source 176 (e.g. battery power, mains power, or the like), a data store 188, and a one or more logic modules, such as a calibration logic 178, a pressure mapping logic 180, a fluid output logic 184, and a communications logic 186.

In some embodiments, the calibration logic 178 may be configured to calibrate one or more of the sensor array 162, the fluid output logic 184, the pressure mapping logic 180, or combinations thereof, optionally before a fluid is disposed within the fluid collecting bag 142. As such, the calibration logic 178 can determine a "zero" weight of the collection bag 142, i.e. a weight of an empty collection bag 142. In an embodiment, the calibration logic 178 can determine an angle of an axis of the hook 132, relative to a transverse axis.

In an embodiment, the pressure mapping logic 180 can determine a difference in pressure from one or more sensors 160 of the sensor array 162 and can determined an axis of force applied to the sensor array 162 relative to a transverse axis. As such, the pressure mapping logic 180 can determine if the direction of force from the collection bag 142 is "on-axis" i.e. parallel to a transverse axis, or is "off-axis" i.e. is at an angle of the transverse axis. Further, the pressure mapping logic 180 can determine a degree of angle of off-axis force, and a direction of off-axis force, i.e. longitudinal, lateral or at an angle therebetween.

In an embodiment, the fluid output logic 184 can be configured to receive one or more signals from the sensor array 162 (e.g. a pressure value from a pressure sensor 160) and determine a change in weight of the collection bag 142 over time. As such, the fluid output logic 184 can determine a volume of fluid within the collection bag 142 and change in fluid volume over time to determine a fluid flow rate. In an embodiment, the fluid output logic 184 can receive information from the pressure mapping logic 180 to determine changes in pressure that may occur from off-axis loading and can modify the data to mitigate errors that may occur from off-axis loading. Advantageously, the fluid output logic 184 can determine off-axis loading in three-dimensional space, from the pressure sensor array alone and without the need for a tilt sensor, gyroscope, or accelerometer that can be easily affected by vibrations or shock damage during movement or transport.

In an embodiment, calibration data, fluid output data, (i.e. fluid volume, flow rates, associated date/time stamps, etc.), pressure-mapping data, (i.e. on-axis data, off-axis data, etc.), combinations thereof, or the like, can be stored to the data store 188. In an embodiment the data can be encrypted. In some embodiments, the communications logic 186 may be configured to communicate information between the console 170 and one or more of the network 90 and external computing device 80 (e.g. EHR) via a message, or the like. In an embodiment, one or more logic engines, e.g. calibration logic 178, pressure mapping logic 180, fluid output logic 184, communications logic 186, or the like can use predetermined rule sets, machine learning algorithms, artificial intelligence (AI), neural networks, or the like to perform one or more functions as described herein.

In an embodiment, information about the system 100, the fluid drainage system 140, patient information, clinician information, combinations thereof can be entered and stored to the data store 188, using one or more logic engines. In an embodiment, such information can be retrieved by the system 100 from the network 90 and one or more external computing devices, e.g. EHR 80, and stored to the data store 188. Exemplary system information about the system 100 can include make, model, serial numbers, part numbers, technical specifications or the like about one or more components of the system 100. Exemplary information about the fluid drainage system can include make, model, serial numbers, part numbers, technical specifications or the like about the catheter, drainage tube, or collection bag 142, e.g. a maximum volume of the collection bag 142. Exemplary information about patient or clinician can include name, date of birth patient health records, clinician employee records, or the like.

In an embodiment, the hanger 130 can be a single-use hanger 130 and the console 170 can be activated when the collection bag 130 is coupled with the hook 132, or when the securement ball 134 engages the socket 118. Activating the console 170 can include entering patient data, clinician data, fluid volume data, or calibrating the hanger 130. In an embodiment, the collection bag 142 can be formed integrally with the hanger 130.

In an embodiment, the fluid output logic 184 can compare a current fluid volume metric within the collection bag 142 and compare it with the maximum fluid volume metric of the collection bag 142. If the current fluid volume metric is approaching the maximum volume metric of the fluid collection bag 142, the communications logic 186 can transmit a message to a clinician or external computing device 80, by way of the network 90.

In an embodiment, the console 170 is configured to detect the one or more measured pressure values from the one or more sensors 160 in the sensor array 162. In some embodiments, the measured pressure values may be stored in the pressure mapping data store 188. The measured pressure values may be configured to be correlated to a fluid output volume value that corresponds to a volume of fluid collected within the fluid collecting bag 142. The fluid output volume value may be paired with a time of day value, corresponding to the hour and minute of the day the corresponding pressure value was detected in the time of day value, fluid output volume value pairing. The console 170 may be configured to store each time of day value, fluid output volume value pairing within the fluid output volume value data store 190. In some embodiments, the console 170 may be configured to display each time of day value, fluid output volume value pairing as it is determined.

In some embodiments, the system 100 may be configured to detect pressure values from the sensor array 162 at regular timed intervals (e.g., every five minutes, every hour, every 30 seconds, or the like). In some embodiments, the system 100 may be configured to detect pressure values from the sensor array 162 at user defied time intervals. In an embodiment, a user may define how many fluid output volume values the console detects in a specific time period. By way of a non-limiting example, the user may desire six (6) fluid output volume values in an hour and the system 100 may be configured to detect one fluid output volume value every ten (10) minutes.

In some embodiments, wherein the console 170 is located within the hanger 130, the hanger 130 may be configured to store additional data or information. For example, the fluid collecting bag hanger 130 or the console 170 may be configured store output fluid flow information, system information, patient information, or the like. Output fluid flow information can include current or historical output fluid volume information, output fluid flow information (i.e. change in volume over time, rate of change in volume over time), or the like. System information can include the make, model, serial number, etc. of the fluid collecting bag hanger 130, the system, the console 170, components thereof, or the like. Patient information can include height, weight, blood pressure, etc. of the patient, or similar health record information. Advantageously, the fluid flow information, system information, patient information, and the like, can be linked to the fluid collecting bag hanger 130, stored on the console 170 and transported with the system 100 and the patient. The fluid collecting bag hanger 130 can then be coupled to a different automatic fluid flow system, e.g. during transport or console malfunction, and continue to measure output fluid flow without losing the historical data, or transferring the data separately. As such, the data remains with the patient and the system 100 and is not lost when a patient is moved or the console 170 malfunctions.

Figure 5A:
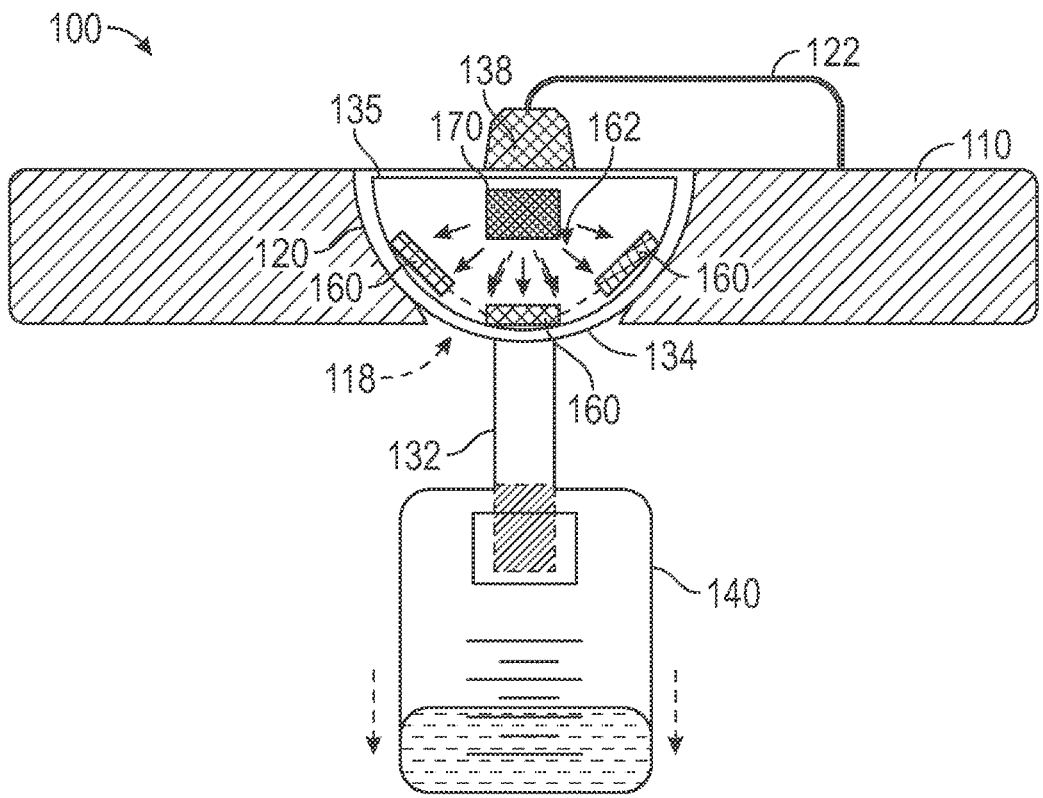
FIGS. 5A-5B illustrate an exemplary method of use for a fluid monitoring system, in accordance with embodiments disclosed herein.
Figure 5B:
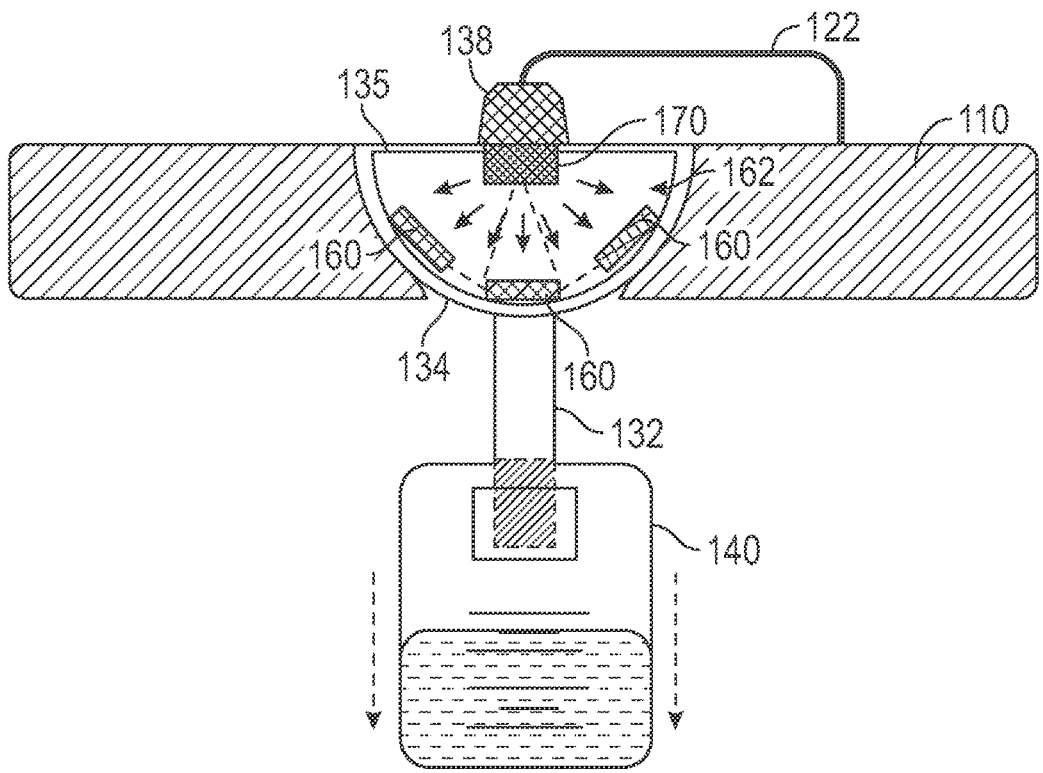

FIGS. 5A-5B illustrate an exemplary method of measuring fluid output using the automated weight based fluid output monitoring system 100, in accordance with some embodiments. In some embodiments, the fluid collecting bag 142 is coupled to the hook 132, wherein the hook 132 is extending transversely through the channel 116. The fluid collecting bag 142 is in fluid communication with the catheter 146. The securement ball 134 is engaged with the socket 118 of the stand 110. The sensor array 162 is communicatively coupled to the console 170 through the port 138 by the connector 122.

As illustrated in FIG. 5A, the fluid output collected from a patient fills a volume within the fluid collecting bag 142. The volume of the fluid creates pressure on the hook 132 and the securement ball 134. The pressure of the hook 132 creates pressure on the one or more sensors 160 in the sensor array 162 that is detected, measured as a first pressure value and transmitted to the console 170. The console 170 receives the pressure value that is correlated with a fluid output volume value. The fluid output volume value is paired with a time of day value in a first time of day value, fluid output volume value pairing. The first time of day value, fluid output volume value pairing is stored on the console 170, displayed on the computing device or a combination thereof.

As illustrated in FIG. 5B, as the volume of the output fluid within the fluid collecting bag 142 increases, the weight of the fluid collecting bag 142 increases, created an increased pressure on the one or more sensors 160 in the sensor array 162 that is detected and measured at the one or more sensors 160 as a second pressure value. The second pressure value is transmitted to the console 170 where it is correlated with a second fluid output volume value as a second time of day value, fluid output volume value pairing. The console 170 can determine an increase in fluid output volume within the fluid collecting bag 142 by determining a difference between the first time of day value, fluid output volume value pairing and the second time of day value, fluid output volume value pairing. The console 170 may be configured to transmit the difference between the first pairing and second pairing to a display, the computing device or the like.

Figure 6:
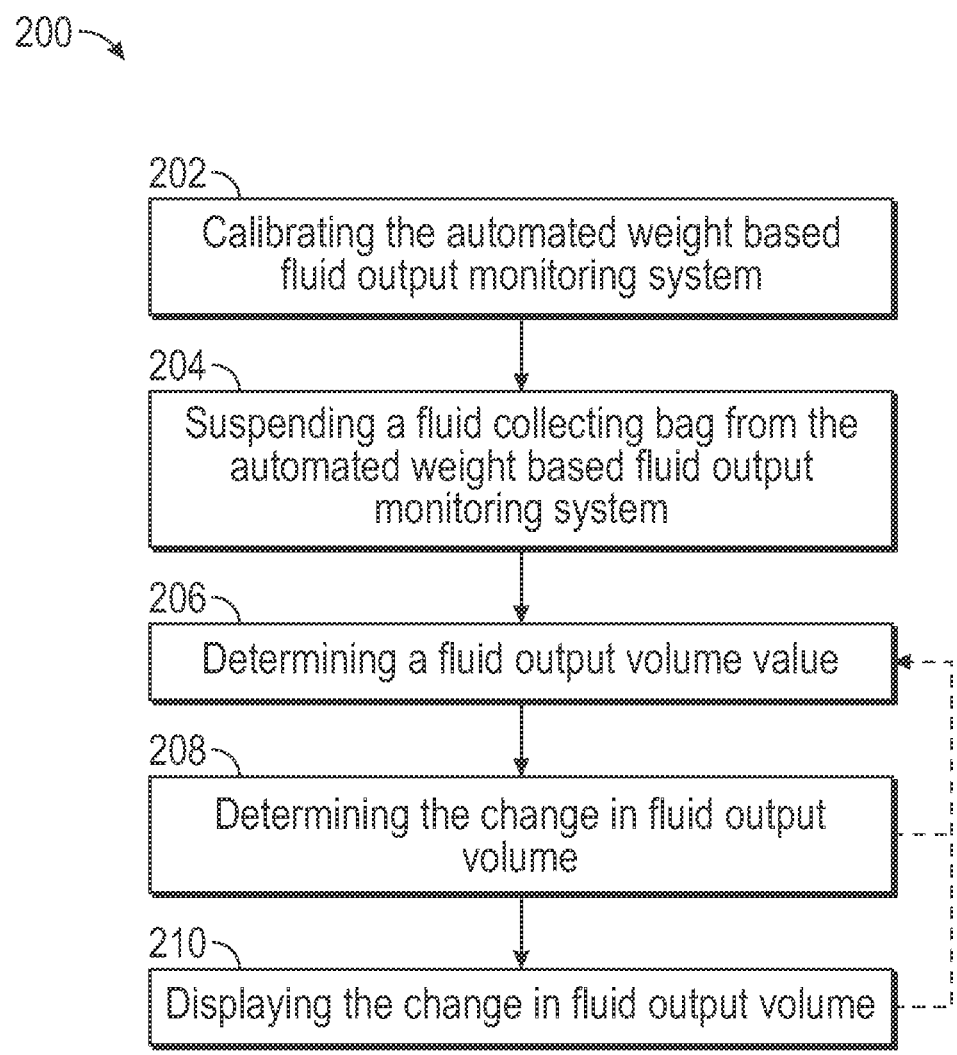
FIG. 6 illustrates a flow chart of an exemplary method of use for a fluid monitoring system, in accordance with embodiments disclosed herein.

FIG. 6 illustrates a flow chart of the exemplary method of measuring fluid output using the automated weight based fluid output monitoring system. In some embodiments, the method 200 includes calibrating the automated weight based fluid output monitoring system 100 (block 202). In some embodiments, calibrating includes activating the calibration logic 178. In some embodiments, the method 200 includes suspending the fluid collecting bag 142 from the hook 132 (block 204). In some embodiments, the fluid collecting bag 142 may be in fluid communication with a catheter. In some embodiments, the method 200 further includes determining a fluid output volume value (block 206). In some embodiments, determining includes using the sensor array 162 to detect one or more pressure values of the fluid collecting bag 142 on the hook 132. The pressure values are transmitted to the console 170. The console 170 may correlate the one or more pressure values with one or more fluid output volume values and one or more time of day values in a time of day value, fluid output volume value pairing. The method 200 further includes determining the change in fluid output volume within the fluid collecting bag (block 208). In some embodiments, determining includes determining the change in fluid output volume over a time interval. In some embodiments, the time interval may be user-specified. In some embodiments, determining includes determining the change between two or more fluid output volume-time of day pairings. For example, determining the change may include determining the change in fluid output volume between a first time of day value, fluid output volume value pairing and a second time of day value, fluid output volume value pairing.

In some embodiments, the first pairing may include the first measured pairing and the second pairing may include any subsequent measured pairing. In some embodiments, the first pairing may include any measured pairing and the second pairing may include any measured pairing after the first pairing. After determining the change in fluid output volume within the fluid collecting bag, the system 100 may be configured to determine a new fluid output volume value and generate a new time of day value, fluid output volume value pairing and determine the change in fluid output by determining the change between the previous pairing and the new pairing. The method 200 further includes displaying the change in fluid output volume (block 210). In some embodiments, displaying includes displaying the fluid output volume on a display, a computing device 80 e.g. an EHR system. In some embodiments, after displaying the change in fluid output volume, the method 200 may optionally include determining a new fluid output volume value, determining the new change in fluid output volume and displaying the new change in fluid output volume. In some embodiments, the system 100 may determine a new fluid output volume value, determine the new change in fluid output volume and display the new change in fluid output volume at automatically defined or user defined time intervals. In some embodiments, the method 200 may include displaying the change in fluid output volume over time.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An automated fluid monitoring system, comprising:
   a stand including a socket extending along a transverse axis;
   a hanger having a securement ball defining a semi-spherical shape and including a hook extending therefrom along a first axis, the hook coupled with a fluid collection bag, the securement ball configured to rotatably engage the socket; and
   a sensor array disposed on a surface of the securement ball and configured to detect a change in pressure between the hanger and the stand, and to detect an angle of pressure along the first axis, relative to the transverse axis.

2. The automated fluid monitoring system according to claim 1, wherein the sensor array includes one or more pressure sensors disposed on the surface of the securement ball.

3. The automated fluid monitoring system according to claim 1, wherein the socket is configured to engage the securement ball to prevent linear movement along a longitudinal axis and a lateral axis and allow the first axis of the hook to pivot relative to the transverse axis.

4. The automated fluid monitoring system according to claim 1, wherein the socket defines a semi-spherical concave shape.

5. The automated fluid monitoring system according to claim 1, further including a console including one or more processors, an energy source, a data store, a calibration logic, a pressure mapping logic, and a fluid output logic.

6. The automated fluid monitoring system according to claim 5, wherein the console is disposed within the hanger and communicatively coupled with one of the stand, a network, an external computing device, or an electronic health record system.

7. The automated fluid monitoring system according to claim 5, wherein the console is disposed within the stand and is communicatively coupled with the sensor array by way of a connector wire or a port disposed on the hanger.

8. The automated fluid monitoring system according to claim 5, wherein the console is disposed remotely from both the hanger and the stand as a stand-alone device and is wirelessly communicatively coupled with the sensor array.

9. The automated fluid monitoring system according to claim 5, wherein the fluid output logic is configured to receive a signal from the sensor array and determine a fluid volume within the fluid collection bag, or a change in fluid volume within the fluid collection bag over time.

10. The automated fluid monitoring system according to claim 5, wherein the pressure mapping logic is configured to receive a signal from the sensor array and determine an angle of the first axis relative to the transverse axis.

11. The automated fluid monitoring system according to claim 5, wherein the calibration logic is configured to receive a signal from the sensor array and calibrate one or more of the sensor array, the fluid output logic and the pressure mapping logic.

12. The automated fluid monitoring system according to claim 1, wherein the fluid collection bag is in fluid communication with a catheter and configured to drain a fluid from a bladder of a patient.

13. The automated fluid monitoring system according to claim 1, wherein the hanger further includes a stabilizing handle configured to engage one of a medical bed, a door, or an intravenous pole.

14. The automated fluid monitoring system according to claim 1, wherein the hook is selectively detachable from the hanger.

15. A method of measuring a fluid output from a patient, comprising:
   coupling a spherical surface of a securement ball of a hanger with a concave socket of a stand, the socket defining a transverse axis and allowing the hangar to pivot about the transverse axis relative to the stand;
   coupling a fluid collection bag with a hook of the hanger, the hook extending along a first axis;
   applying a force to the hanger along the first axis;
   detecting a change in pressure between the securement ball and the socket;
   determining a volume of fluid within the fluid collection bag; and
   determining an angle of the first axis relative to the transverse axis.

16. The method according to claim 15, wherein the spherical surface includes a sensor array including one or more pressure sensors.

17. The method according to claim 15, wherein the securement ball engages the socket to prevent linear movement of the hanger along a longitudinal axis or a lateral axis.

18. The method according to claim 15, wherein determining the volume of fluid or determining the angle of the first axis is performed by a console disposed within the hanger and including one or more of a processor, an energy source, a data store, a calibration logic, a pressure mapping logic and a fluid output logic.

19. The method according to claim 15, wherein determining the volume of fluid or determining the angle of the first axis is performed by a console disposed within the stand and communicatively coupled with the hanger, the console including one or more of a processor, an energy source, a data store, a calibration logic, a pressure mapping logic, and a fluid output logic.

20. The method according to claim 15, further including determining a change in fluid volume within the fluid collection bag over time using a fluid output logic.

21. The method according to claim 15, wherein applying the force to the hanger along the first axis includes draining a fluid from the patient into the fluid collection bag, the fluid collection bag in fluid communicating with a Foley catheter.

\* \* \* \* \*